(12) United States Patent
Piercey et al.

(10) Patent No.: US 11,530,203 B2
(45) Date of Patent: Dec. 20, 2022

(54) TETRAZOLE AZASYDNONE

(71) Applicant: Purdue Research Foundation, West Lafayette, IN (US)

(72) Inventors: Davin Glenn Piercey, Lafayette, IN (US); Matthew Lee Gettings, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/340,151

(22) Filed: Jun. 7, 2021

(65) Prior Publication Data

US 2022/0073502 A1 Mar. 10, 2022

Related U.S. Application Data

(60) Provisional application No. 63/066,850, filed on Aug. 18, 2020.

(51) Int. Cl.
*C07D 413/04* (2006.01)

(52) U.S. Cl.
CPC .................. *C07D 413/04* (2013.01)

(58) Field of Classification Search
CPC .................................................... C07D 413/04
See application file for complete search history.

(56) References Cited

U.S. PATENT DOCUMENTS 5,889,161 A * 3/1999 Bottaro ................ C07D 207/50
149/55

\* cited by examiner

*Primary Examiner* — Kamal A Saeed
(74) *Attorney, Agent, or Firm* — Purdue Research Foundation

(57) ABSTRACT

The present disclosure relates to a novel tetrazole azasydnone, a method of making the novel tetrazole azasydnone, and a method of using the novel tetrazole azasydnone as a primary explosive. In one aspect, the novel tetrazole azasydnone has a structure of formula I:

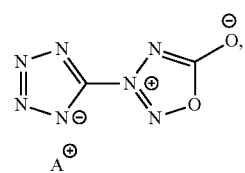

wherein $A^{\oplus}$ represents a cation with a $1^+$ charge.

4 Claims, 2 Drawing Sheets

TETRAZOLE AZASYDNONE

CROSS-REFERENCE TO RELATED APPLICATION

This application claims the priority benefit of U.S. Provisional Patent application No. 63/066,850, filed Aug. 18, 2020, which is incorporated herein by reference in its entirety.

GOVERNMENT RIGHTS

This invention was made with government support under Award No. W911NF-18-1-0463 awarded by the Army Research Office. The government has certain rights in the invention.

TECHNICAL FIELD

The present disclosure relates to a novel tetrazole azasydnone, a method of making the novel tetrazole azasydnone, and a method of using the novel tetrazole azasydnone as a primary explosive.

BACKGROUND

This section introduces aspects that may help facilitate a better understanding of the disclosure. Accordingly, these statements are to be read in this light and are not to be understood as admissions about what is or is not prior art.

The synthesis of high-energy density materials is important in the design of explosive materials. While much attention has been placed on the synthesis of secondary explosives, the synthesis of materials that fit into the primary explosive category receives significantly less attention. Primary explosives, however, are ubiquitous, as they are present in detonators and percussion primers. These systems are important ignition train energy systems that convert mechanical stimuli into rapid chemical energy to ignite many small-, medium- and large caliber explosive and propellant munitions found in both military and commercial sectors. Although mercury, lead and silver fulminate were early primary explosives employed in detonators and primers. These systems are important ignition train energy systems that convert mechanical stimuli into rapid chemical energy to ignite many small-, medium- and large caliber explosive and propellant munitions found in both military and commercial sectors. Although mercury, lead and silver fulminate were early primary explosives employed in detonators and primers, these materials are no longer used due to their inherent instability and hypersensitivity. Today, in-service detonator and primer mixtures contain significant amount of lead azide and/or lead styphnate. While the compounds function reliably, lead is a well-documented toxin to both the environment and human health. Lead has been found to be present in significant numbers on many military and civilian firearm training facilities, and the US Environmental Protection Agency has called for strict limits on these ranges in an effort to protect the groundwater supply, environmental and human health.

Driven by the EPA regulations and the need to protect and improve human and environmental health, recent efforts have been devoted toward developing lead-free primary explosive alternatives. Two such compounds that have been subject to intense investigation is the copper-based material DBX-1 and the metal-free triazine triazide (TTA) (FIG. 1). Sec J. J. Sabatini, K. D. Oyler, *Crystals* 2016, 6, 1-22. While copper has been shown to be a significant improvement over lead, it is still plagued by toxicity issues, and the current synthesis of DBX-1 is problematic. Due to its metal-free nature, TTA would be an ideal primary explosive candidate due to its low toxicological profile. Unfortunately, TTA is classified as a hyper-primary, is very dangerous to isolate and handle, and has been shown to sublime at temperatures commonly encountered during processing of primary explosive mixtures. Thus, there remains a continued interest in developing high-energy primary explosive materials that are capable of being handled safely, while still possessing low toxicity and possessing enough sensitivity to undergo reliable detonation when desired.

High-nitrogen heterocycles make up the backbone of many energetic materials. Heterocycles such as tetrazoles, tetrazines, triazoles and triazines have all found extensive use in the design of new energetic materials. Their nitrogen content contributes to the energetic properties of these materials due to high heats of formation as a result of the thermodynamic driving force of nitrogenous compounds towards the formation of nitrogen gas. Having an appropriate oxygen balance (enough oxygen in the molecule to oxidize C and H to $CO_2$, CO and $H_2O$) also contributes to energetic output, and for compounds possessing ring or cage strain, this can further contribute energy to the final energetic material. Unfortunately, high nitrogen heterocycles have some disadvantages in energetic materials; in some cases, as nitrogen content increases, sensitivities increase, and increasing nitrogen content can also decrease the opportunity to functionalize the molecule. For example, in tetrazole-based energetic materials, oxygen balances are often low as a result of the tetrazole ring only having (usually) two accessible sites for functionalization and incorporation of oxidizing moieties. The density of an energetic material is an important factor affecting final performance of the energetic material, and as the number of N—N bonds increase, the number of polarized bonds can decrease, reducing molecular motivation for crystal packing in high-density arrangements.

Energetic materials containing zwitterionic and charged structures are an important method of increasing density, and in some cases stability of energetic materials. Incorporating these charged structures allows high-density materials to form based on high-nitrogen backbones through the introduction of charged structures. For example, when diamino-dinitropyrazine is oxidized to its oxide, LLM-105, the introduction of zwitterionic N-oxide results in improved density and energetic performances. N-oxides are not the only method of introducing a zwitterionic system to energetic material, and N-nitroimides, and nitrodiazine oxides have all been used to prepare high-performing, dense, energetic materials.

In order to improve simultaneously the oxygen balance, and density of high-nitrogen energetic materials, one can also introduce an oxygen atom within the ring. This may have the advantage of increasing oxygen balance and setting up polarized bonds allowing high densities. While this strategy has been very well explored in the 2-carbon 5-membered heterocycles with oxadiazole-based energetic materials, introducing an oxygen to a 5-membered 1-carbon heterocycle is less explored as an energetic backbone. (FIG. 2).

Therefore, there is a need for novel materials to be used as primary explosives.

SUMMARY

The present disclosure relates to a novel tetrazole azasydnone, a method of making the novel tetrazole azasydnone, and a method of using the novel tetrazole azasydnone as a primary explosive.

In one embodiment, the present disclosure provides a novel tetrazole azasydnone compound of Formula I:

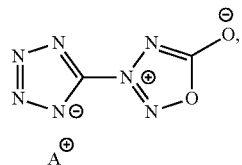

wherein A⊕ represents a cation with a 1+ charge.

DETAILED DESCRIPTION

Figure 1:
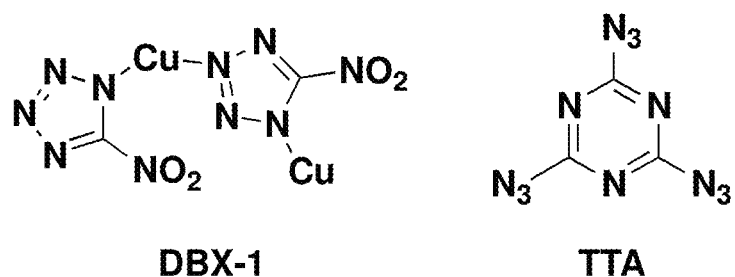
FIG. 1 illustrates structures of copper(I) 5-nitrotetrazolate (DBX-1) and 2,4,6-azido-1,3,5-triazine (TTA).
Figure 2:
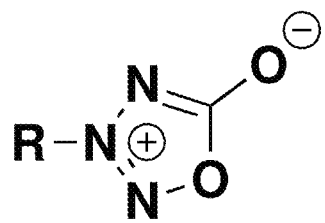
FIG. 2 illustrates structure of Azasydnone.

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

An azasydnone can be considered as a tetrazole in which a ring nitrogen has been replaced by an oxygen, with an additional exocyclic oxygen on the carbon atom. This means they are an oxygen-balanced hybrid of azide and $CO_2$, and when functionalized on the ring nitrogen also adopt a zwitterionic structure. Despite having these molecular features conducive to high performance, they have been much less studied as energetic materials.

In this disclosure an azasydnone ring on the 5-position of the tetrazole ring has been prepared to provide tetrazole azasydnone. Several energetic salts of this structure were also prepared. These energetic materials were characterized by X-ray diffraction, infrared spectroscopy, NMR spectroscopy, and DSC. Computational calculations predicting energetic performance confirm exceedingly high energetic properties of this class of materials. This disclosure has demonstrated the ability of this unique class of compounds to be used as a backbone of high-performing energetic materials and novel primary explosives.

To an acidic solution of 5-aminotetrazole in water was added sodium nitrite forming a solution of the EXTREMELY SENSITIVE diazotetrazole. Large dilutions of water (200 ml): 5-aminotetrazole (800 mg) were used for this step of the synthesis given that crystals of diazotetrazole are known to detonate upon crystallization. To this solution was added bromonitromethane and the solution stirred overnight forming hydrazone 2 (Scheme 1). Hydrazone 2 was extracted into ethyl acetate and evaporated. Ring closure of hydrazone 2 to tetrazole azasydnone was performed in dioxane by stirring over solid ammonium nitrate until full conversion of 2 to azasydnone 3. After cyclization, the reaction was evaporated and the resultant oil re-dissolved in water leaving an oily residue and solution of tetrazole azasydnone (3) in water. Strong acidification of the solution with nitric acid after filtration and discarding of the oily solids allowed extraction of pure 3 into ethyl acetate.

Scheme 1. Synthesis of Example 1: TAZ (3)

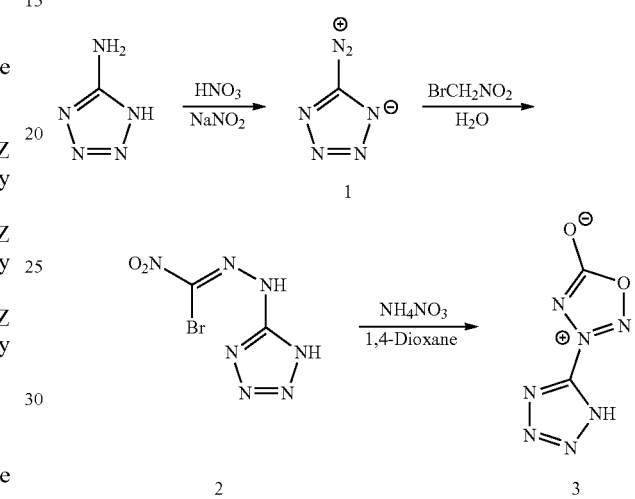

From either pure solution of tetrazole azasydnone or the aqueous filtrate, the ammonium (4), hydrazinium (5) and triethylammonium (6) salts of 3 were prepared by simply adding the aqueous base until the solution was slightly basic. Evaporation of the solution and recrystallization gave pure salts. (Scheme 2).

Scheme 2. Synthesis of TAZ salts 4-6 from 3

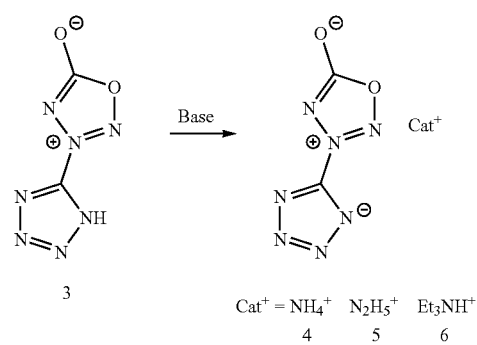

Reaction of 4 with aqueous silver nitrate precipitated the silver salt 7 which detonates with violence upon flame-test (Scheme 3). Video of detonation of 7 against a copper plate available at www.davinpiercey.com/AgTAZdet.

Scheme 3. Synthesis of TAZ salt 7 from 4

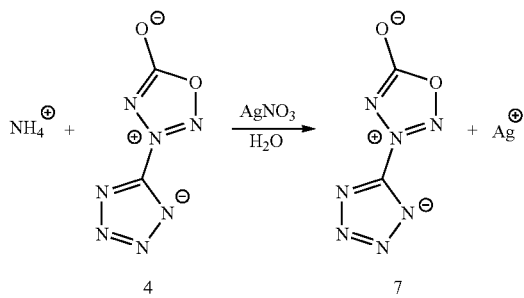

To prepare additional energetic compounds, butylammonium salt (8) was prepared from 3 in aqueous solution, extracted into ethyl acetate and evaporated giving oily 8. Butylammonium salt 8 was run through Amberlyst 15™ ion exchange resin loaded with the appropriate cation to obtain hydroxylammonium (9), guanidinium (10), aminoguanidinium (11) and triaminoguanidinium (12) tetrazoleazasydnones. (Scheme 4).

Scheme 4. Synthesis of TAZ salts 5, 9-12 from 8

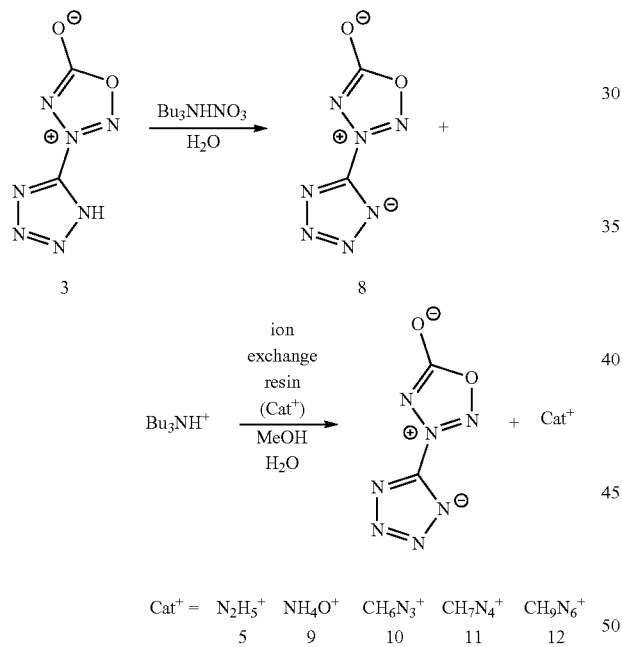

After evaporation of water, while hydroxylammonium (9) and guanidinium salts (10) were isolated pure, triaminoguanidinium and aminoguanidinium salts showed extensive decomposition. As all crystal structures were obtained by ether diffusion into a methanolic solution of the salt, we hoped to obtain the non-decomposed azasydnone salt crystal in this manner, but actually obtained a crystal of zwitterionic 2-guanidinium-1-aminocarboxylate monohydrate. This supports the hypothesis that the more nucleophilic triamino and aminoguanidinium cations are attacking the C on the azasydnone, eliminating azidotetrazole. To confirm this, the addition of ammonium azidotetrazolate to a NMR tube containing partially-decomposed aminoguanidinium tetrazoleazasydnone showed the suspected azidotetrazolate peak increase (Scheme 5).

Scheme 5. Decomposition of 11, forming azidotetrazole and zwitterionic 2-guanidinium-1-aminocarboxylate monohydrate

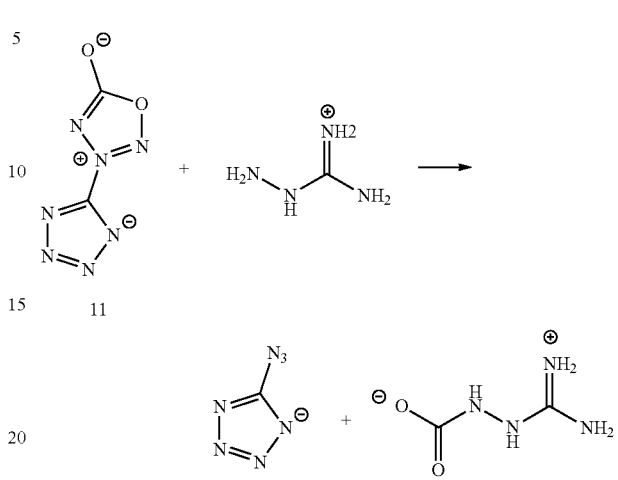

Figure 3:
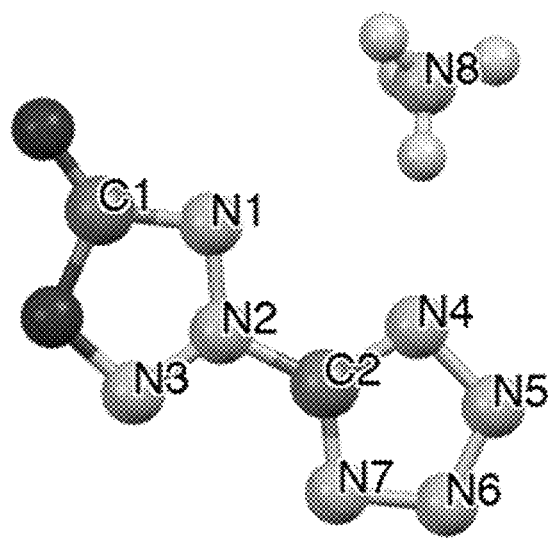
FIG. 3 illustrates molecular unit of ammonium TAZ (compound 4). Ellipsoids are drawn at the 50% probability level.
Figure 4:
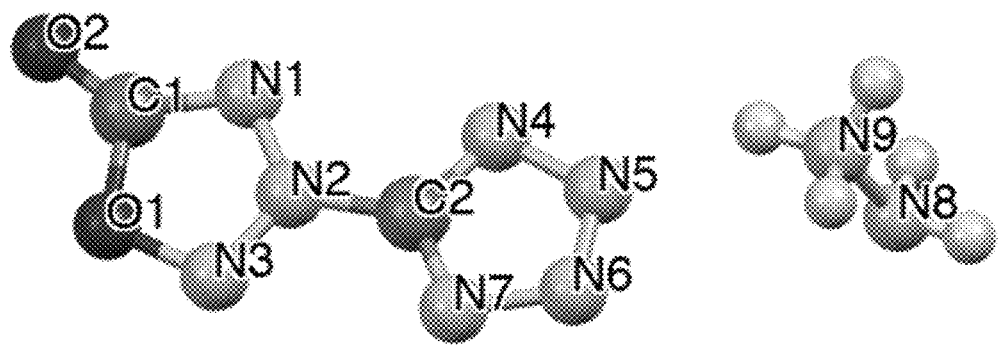
FIG. 4 illustrates molecular unit of ammonium TAZ (compound 5). Ellipsoids are drawn at the 50% probability level.
Figure 5:
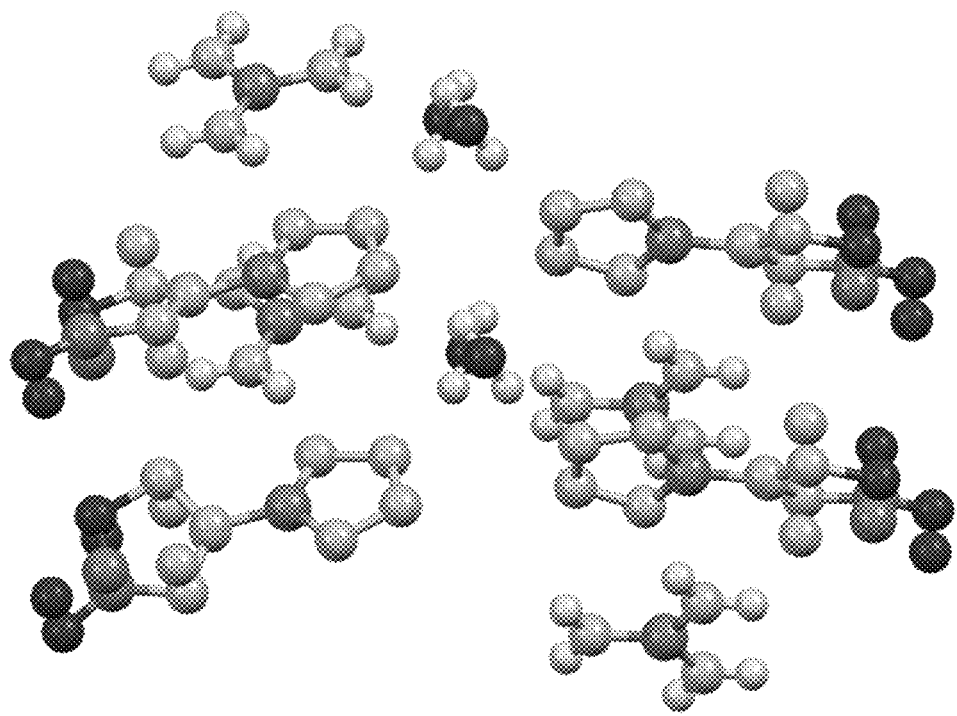
FIG. 5 illustrates molecular unit of ammonium TAZ (compound 10). Ellipsoids are drawn at the 50% probability level.

Compounds 9, 11, and 12 were also attempted to be prepared by reaction of silver salt 7 with the corresponding chloride salt in water, followed by filtration of silver chloride and evaporation to obtain products. In the case of 9 this improved yield, and in the case of 11 and 12, the same decomposition forming azidotetrazole was seen. (Scheme 6) The crystal structures for 4, 5, and 10 are shown in FIG. 3 to FIG. 5.

Scheme 6. Synthesis of TAZ salts 9, 11 and 12 from 7. Salts 11 and 12 underwent partial decomposition

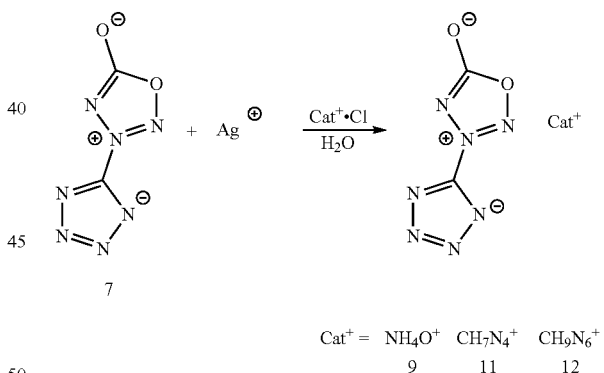

The salts of tetrazoleazasydnone may also be compared with their nitrotetrazole and azidotetrazole analogs. All TAZ salts had greater densities than analogous azidotetrazoles. Densities of 4, 5, and 10-12 exceeded their nitrotetrazole analogs and 3 exceeded the density of RDX (1.820 g/cm³). This indicates, that overall as an explosophore in energetic materials, that the azasydnones should be considered as important as the ubiquitous nitro group given the high probability of being higher density, which is one of the most crucial determinants of explosive performance.

Of all TAZ compounds prepared, the metal-free primary explosive 3 and silver salt 7 are the best candidates to serve as a primary explosive replacement. The toxicity of lead underscores the importance of removing lead from primary explosive mixtures. Table 1 compares these primary explosives to sensitivities and performances of triazine triazide (TTA), DBX-1, lead styphnate, and lead azide.

TABLE 1

Sensitivities and performance of 3 and 7 compared to TTA, DBX-1, lead azide (LA), and lead styphnate (LS)

| Compound | 3 | TTA | 7 | DBX-1 | LA | LS |
|---|---|---|---|---|---|---|
| IS [J] | 2 | <2.5 | 3 | 0.036 | 2.5-4 | <2.5 |
| FS [N] | 10 | 0.1 | 14 | 0.1 | 0.1-1 | 0.1 |
| $T_{dec}$ [° C.] | 160 | 187 | 150 | 337 | 315 | 282 |
| $\rho$ [g · cm$^{-3}$] | 1.84 | 1.54 | — | 2.58 | 4.80 | 3.00 |
| $P_{CJ}$ [kbar] | 327 | — | — | — | 8330 | — |
| $V_{det}$ [m · s$^{-1}$] | 8906 | 6900 | — | ~7000 | 5300 | 4900 |

The free acid (3) and silver (7) salts were more sensitive than RDX (7 J, 120 N). (Table 2) Among TAZ compounds, 3 had best detonation performance (327 kbar, 8906 m/s), comparable to RDX (336 kbar, 8801 m/s). The free acid 3 had the highest heat of formation, which despite its lower nitrogen content, had the greatest calculated density.

TABLE 2

Energetic properties of prepared compounds. Calculated densities shown when X-ray diffraction densities were unavailable.

| | 3 | 4 | 5 | 7 | 9 | 10 | 11 | 12 | RDX* |
|---|---|---|---|---|---|---|---|---|---|
| Formula | $C_2HN_7O_2$ | $C_2H_4N_8O_2$ | $C_2H_5N_9O_2$ | $Ag \cdot C_2N_7O_2$ | $C_2H_4N_8O_3$ | $C_3H_6N_{10}O_2$ | $C_3H_7N_{11}O_2$ | $C_3H_9N_{13}O_2$ | $C_3H_6N_6O_7$ |
| FW [g mol$^{-1}$] | 155.08 | 172.11 | 187.12 | 261.94 | 188.11 | 214.15 | 229.16 | 259.19 | 222.12 |
| IS [J] $^a$ | 2 | >40 | >40 | 3 | >40 | >40 | >40† | 1† | 7.5 |
| FS [N] $^b$ | 10 | >360 | >180 | 14 | >360 | >360 | >360† | >64† | 120 |
| N [%] $^c$ | 63.23 | 65.11 | 67.37 | 37.43 | 59.57 | 60.33 | 67.23 | 70.25 | 37.84 |
| $\Omega$ [%] $^d$ | −25.79 | −37.18 | −38.47 | −15.27 | −25.52 | −48.24 | −52.36 | −52.47 | −21.6 |
| $T_{dec}$ [° C.] $^e$ | 160 | 155 | 155 | 150 | 130 | 151 | 150† | 160† | 205 |
| $\rho$ [g · cm$^{-3}$] $^f$ | ND | 1.716 | 1.750 | ND | ND | 1.598 | ND | ND | 1.858 |
| $\rho$ [g · cm$^{-3}$]$^{calc}$ | 1.842 | 1.744 | 1.694 | — | 1.796 | 1.655 | 1.654 | 1.642 | — |
| $\Delta_f H°$ [kJ · kg$^{-1}$] $^g$ | 2698.1 | 1372.9 | 2044.3 | — | 1467.2 | −129.41 | 1366.4 | 2051.6 | 316.55 |
| EXPLO5 V6 | | | | | | | | | |
| $-\Delta_{Ex}U°$ [kJ · kg$^{-1}$] $^h$ | 4999.4 | 3873.8 | 4458.7 | — | 4767.1 | 2859.9 | 3410.0 | 4003.4 | 5740 |
| $T_{det}$ [K] $^i$ | 3841.3 | 2907.7 | 3112.2 | — | 3383.4 | 2238.1 | 2540.5 | 2762.7 | 3745 |
| $P_{CJ}$ [kbar] $^j$ | 326.911 | 249.018 | 292.232 | — | 312.423 | 206.739 | 224.274 | 254.654 | 336 |
| $V_{Det.}$ [m · s$^{-1}$] $^k$ | 8906.2 | 8222.4 | 8803.9 | — | 8822.7 | 7736.2 | 8009.0 | 8473.7 | 8801 |
| $V_o$ [L · kg$^{-1}$] $^l$ | 763.7 | 845.9 | 870.6 | — | 829.9 | 880.8 | 863.8 | 894.8 | 783 |

ND not determined;
$^a$ impact sensitivity (BAM drophammer (1 of 6));
$^b$ friction sensitivity (BAM friction tester (1 of 6));
$^c$ nitrogen content;
$^d$ oxygen balance ($\Omega = (xO - 2yC - \frac{1}{2}zH)M/1600$);
$^e$ decomposition temperature from DSC ($\beta = 5°$ C.);
$^f$ from X-ray diffraction;
$^g$ calculated heat of formation;
$^h$ energy of explosion;
$^i$ explosion temperature;
$^j$ detonation pressure;
$^k$ detonation velocity;
$^l$ volume of detonation gases (assuming only gaseous products).
*Values based on R. Meyer, J. Köhler, A. Homburg, *Explosives*, Wiley-VCH & Co. KGaA, Weinheim, 2007, and the EXPLO5 V6 database.
†11 and 12 showed evidence of decomposition forming azidotetrazole.

Compound 3 is a metal-free primary explosive which can be safely handled unlike TTA, which suffers from sublimation issues and hyper primary sensitivity. Although 3 and 7 have lower densities than the in-service lead salts (lead azide, lead styphnate), less of the metal-free compound (3) is required to attain the gas generation necessary for a primer composition in the formulation mixture. Removal of the metal entirely remains a critical goal due to the inherent toxicity of lead. While it is true that the decomposition temperatures of lead azide and lead styphnate are higher than 3, lower decomposition temperatures are tolerated in primer compositions. Tetrazene, a known and ubiquitous sensitizer in primary explosive mixtures, has a decomposition temperature of 118.6° C. Thus, decomposition temperatures of 150-160° C. are tolerable.

The silver salt (7) also has a reasonable sensitivity with respect to primary explosive power. The impact sensitivity of 7 is similar to PETN (3 J), while remaining sensitive to friction. Silver salts enjoy very high densities, which allows sufficient amount of material to fit into a primer cup (i.e. usually only accommodates 30-40 mg of mixture). Silver salts, like copper-based primaries (e.g. DBX-1) are significantly less toxic than lead and will likely have lower toxicity than lead-based energetic compounds.

Experimental Details

General Methods. All reagents and solvents were used as received (Sigma-Aldrich, Fluka, Acros Organics, Fisher Scientific Co LLC) if not stated otherwise. Alfa Aesar Amberlyst®15H, ion exchange resin, pale brown beads, Styrene-DVB, strongly acidic macroreticular resin was used to exchange cations during synthesis. Melting and decomposition points were measured with a TA Instruments SDT Q600 TGA/DSC using heating rates of 5° C.·min$^{-1}$. $^1$H and $^{13}$C NMR spectra were measured with a Bruker AV-III-400-HD (5 mm BBFO SmartProbe) and Bruker AV-III-500-HD (5 mm BBFO Cryoprobe Prodigy) Advance DRX NMR spectrometers. All chemical shifts are quoted in ppm relative to TMS ($^1$H, $^{13}$C). Infrared spectra were measured with a PerkinElmer Spectrum Two FT-IR spectrometer. Transmittance values are described as "strong" (s), "medium" (m) and "weak" (w). Mass spectra were measured with an Agilent 1260 Infinity II Quaternary LC instrument. Sensitivity data were determined using a BAM (Bundesanstalt für Materialforschung) friction tester (Reichel & Partner Gmbh) and OZM BAM Fall Hammer BFH-10 instrument.

CAUTION! The described compounds 3-12 are energetic materials with sensitivity to various stimuli. While we encountered no issues in the handling of these materials, proper protective measures (face shield, ear protection, body armor, Kevlar gloves, and earthened equipment) should be used at all times.

Crystallographic data (excluding structure factors) for the structures in this paper have been deposited with the Cambridge Crystallographic Data Centre, CCDC, 12 Union Road, Cambridge CB21EZ, UK. Copies of the data can be obtained free of charge on quoting the depository numbers CCDC-1971700 (4), CCDC-1971698 (5), and CCDC-1971699 (10) (Fax: +44-1223-336-033; E-Mail: deposit@ccdc.cam.ac.uk, http://www.ccdc.cam.ac.uk).

Synthesis of Tetrazoleazasydnone (HTAZ) (3). 5-Aminotetrazole monohydrate (800 mg, 7.761 mmol) was dissolved in ice-cold water (5° C.). A separate solution of sodium nitrite (660 mg, 9.6 mmol, 1.25 equiv) was dissolved in ice-cold water, acidified with concentrated nitric acid (15.8 M, 1.84 ml). This nitrous solution was added while cold to the aminotetrazole solution, forming diazo tetrazole (1). After 20 minutes of stirring, bromonitromethane (90%) (1.25 g, 8.93 mmol, 1.15 equiv) was added to the diazo tetrazole solution and allowed to stir overnight, forming the hydrazone compound (2). The hydrazone was extracted into ethyl acetate (3×20 ml) and evaporated. The hydrazone was then dissolved in 1,4-dioxane (70 ml) and ammonium nitrate (800 mg, 10 mmol) was added, and stirred until all of the hydrazone cyclized forming the tetrazole azasydnone (3) as determined by mass spec monitoring. The ammonium nitrate was filtered out of the dioxane solution and evaporated. The dried residue was slurried in water (70 ml) and the dark orange-brown solids filtered off. The impurities in the slightly acidic (pH 3-4) aqueous filtrate were extracted into diethyl ether (3×20 ml). The remaining aqueous solution was further acidified (pH<1) with nitric acid and (3) was extracted into ethyl acetate (3×20 ml). Evaporation of the ethyl acetate solution yielded 430 mg (2.77 mmol, 36%) of 3. DSC: 160° C. (dec.). IR: $\tilde{v}$=3067 (w), 3027 (w), 2985 (w), 2856 (w), 2797 (m), 2152 (w), 1972 (w), 1772 (s), 1546 (m), 1505 (m), 1417 (m), 1321 (m), 1257 (m), 1203 (m), 1180 (m), 1184 (w), 1074 (m), 1023 (s), 984 (m), 833 (s), 743 (s), 734 (s), 573 (m) cm$^{-1}$. $^1$H NMR (500 MHz, [D$_6$]D$_2$O): δ=1.86 (s, 1H, —NH) ppm. $^{13}$C NMR ([D$_6$]D$_2$O): δ=167.3 (1C, —N=C—O—), 156.1 (1C, —N=C—N—) ppm. MS m/z: (ESI−) 154.1 (C$_2$N$_7$O$_2^-$). EA (C$_2$HN$_7$O$_2$, 155.08) calcd: C, 15.49; H, 0.65; N, 63.23%. Found: C, 16.69; H, 1.08; N, 60.77%. BAM impact: 2 J. BAM friction: 10 N.

Synthesis of Ammonium 5-(5-oxido-1,2,3,4-oxatriazol-3-ium-3-yl)tetrazol-1-ide (4). The free acid (3) (315 mg, 2.03 mmol) was dissolved in water, treated with ammonium hydroxide solution (14.8 M, 28%) until pH ~8 and evaporated forming ammonium salt (4), yielding 340 mg (1.98 mmol, 97%) of 4. Crystals were grown by diffusion of diethyl ether in ethanol solution. DSC: 155° C. (dec). IR: $\tilde{v}$=3207 (m), 3016 (m), 2842 (m), 2174 (w), 1944 (w), 1775 (s), 1682 (m), 1614 (w), 1428 (s), 1318 (s), 1266 (s), 1198 (s), 1176 (m), 1150 (m), 1137 (m), 1080 (m), 1026 (m), 980 (m), 825 (m), 745 (s), 728 (m), 573 (w) cm$^{-1}$. $^1$H NMR ([D$_6$]D$_2$O): δ=7.22 (s, broad, 4H, —NH$_4$) ppm. $^{13}$C NMR ([D$_6$]D$_2$O): δ=166.9 (1C, —N=C—O—), 155.8 (1C, —N=C—N—) ppm. MS m/z: (ESI−) 154.1 (C$_2$N$_7$O$_2^-$), m/z: (ESI+) below limits of instrument (NH$_4^+$). EA (C$_2$H$_4$N$_8$O$_2$, 172.11) calcd: C, 13.96; H, 2.34; N, 65.11%. Found: C, 14.36; H, 1.72; N, 58.04%; BAM impact: >40J. BAM friction: >360N.

Synthesis of Hydrazinium 5-(5-oxido-1,2,3,4-oxatriazol-3-ium-3-yl)tetrazol-1-ide (5). The ion exchange resin (see "General" information of Experimental Section above) was soaked in water and rinsed clean. The resin was washed several times with hydrazinium hydrochloride aqueous solution, which loaded the resin with the hydrazinium cation. The resin was rinsed several times with water to remove any residual chloride anions. The resin was loaded into a 50 ml burette with water. Tributylammonium salt (8) (~267 mg, 0.78 mmol) dissolved in methanol was pipetted onto the ion-exchange resin. The post ion-exchange aqueous solution was collected below the burette and purified of unreacted tributylammonium compound via ethyl acetate extractions. After ethyl acetate extractions, the aqueous solution was evaporated under an air stream and dried in a desiccator yielding 86 mg (0.460 mmol, 59%) of 5. Crystals were grown by diffusion of diethyl ether in methanol solution. DSC: 155° C. (dec). IR: $\tilde{v}$=3333 (w), 2909 (m), 2147 (w), 1899 (w), 1820 (s), 1786 (s), 1638 (m), 1592 (m), 1592 (m), 1536 (m), 1495 (m), 1479 (m), 1446 (w), 1322 (s), 1263 (s), 1182 (s), 1026 (m), 968 (s), 907 (w), 810 (s), 742 (s), 715 (s), 571 (w) cm$^{-1}$. $^1$H NMR ([D$_6$]D$_2$O): δ=1.76 (s, broad, 5H, —NH$_2$) ppm. $^{13}$C NMR ([D$_6$]D$_2$O): δ=167.0 (1C, —N=C—O—), 154.7 (1C, —N=C—N—) ppm. MS m/z: (ESI−) 154.1 (C$_2$N$_7$O$_2^-$), m/z: (ESI+) below limits of instrument (N$_2$H$_5$+). EA (C$_2$H$_5$N$_9$O$_2$, 187.12) calcd: C, 12.84; H, 2.69; N, 67.37%. Found: C, 13.87; H, 2.74; N, 66.54%. BAM impact: >40J. BAM friction: >180N.

Synthesis of Triethylammonium 5-(5-oxido-1,2,3,4-oxatriazol-3-ium-3-yl)tetrazol-1-ide (6). The free acid (3) (50 mg, 0.3224 mmol) dissolved in ethanol was treated with triethylamine (32.6 mg, 1 equiv) and evaporated. DSC: ND. IR: $\tilde{v}$=2987 (w), 2705 (w), 2491 (w), 2141(w), 1785 (s), 1473 (m), 1392 (s), 1317 (s), 1257 (s), 1184 (m), 1069 (w), 1035 (m), 1014 (m), 971 (m), 812 (m), 747 (m), 726 (w), 566 (w) cm$^{-1}$. $^1$H NMR ([D$_6$]D$_2$O): δ=2.84 (t, 6H, —NH—CH$_2$—CH$_3$), 0.90 (dd, 9H, —CH$_2$—CH$_3$) ppm. $^{13}$C NMR ([D$_6$]D$_2$O): δ=166.2 (1C, —N=C—O—), 155.9 (1C, —N=C—N—) ppm. MS m/z: (ESI−) 154.1 (C$_2$N$_7$O$_2^-$), m/z: (ESI+) 102.2 (C$_6$H$_{16}$N$^-$). BAM impact: ND. BAM friction: ND.

Silver 5-(5-oxido-1,2,3,4-oxatriazol-3-ium-3-yl)tetrazol-1-ide (7). To an aqueous solution of (4) (324 mg, 1.88 mmol) was added silver nitrate (660 mg, 3.89 mmol, 2.1 equiv.) dissolved in water. The mixture was stirred for 20 minutes at 40° C. while shielded from light. The silver salt (7) precipitated out of solution, was filtered and allowed to dry overnight, yielding 330 mg (1.26 mmol, 67%) of 7. DSC: 150° C. (dec.). IR: $\tilde{v}$=2144 (w), 1805 (s), 1542 (w), 1317 (m), 1277 (s), 1184 (m), 1085 (m), 1032 (w), 977 (w), 808 (m), 740 (m), 727 (m), 566 (w), 548 (w) cm$^{-1}$. MS m/z: (ESI−) 154.1 (C$_2$N$_7$O$_2^-$), m/z: (ESI+) 105.1 (Ag$^+$). BAM impact: 3J. BAM friction: 14N.

Synthesis of Tributylammonium 5-(5-oxido-1,2,3,4-oxatriazol-3-ium-3-yl)tetrazol-1-ide (8). The free acid (3) (430 mg, 2.77 mmol) was treated with 0.5 M tributyl ammonium nitrate solution (15.5 ml) and extracted into ethyl acetate. The ethyl acetate extract was evaporated under an air stream yielding 267 mg (0.78 mmol, 28%) of 8. $^1$H NMR ([D$_6$] CD$_3$CN): δ=3.16 (t, 6H, —NH—CH$_2$—CH$_2$—), 1.71 (tt, 6H, —CH$_2$—CH$_2$—CH$_2$—), 1.34 (dt, 6H, —CH$_2$—CH$_2$—CH$_3$), 0.89 (t, 9H, —CH$_3$) ppm. $^{13}$C NMR ([D$_6$] CD$_3$CN): δ=165.8 (1C, —N=C—O—), 156.7 (1C, —N=C—N—)

ppm. MS m/z: (ESI−) 154.1 ($C_2N_7O_2^-$), m/z: (ESI+) 186.1 ($C_{12}H_{28}N^+$). BAM impact: ND. BAM friction: ND.

Synthesis of Hydroxylammonium 5-(5-oxido-1,2,3,4-oxatriazol-3-ium-3-yl)tetrazol-1-ide (9). The hydroxylammonium salt (9) was made by two methods (A and B).

(method A) The ion exchange resin was loaded with hydroxylammonium hydrochloride following similar steps as the synthesis of 5. Tributylammonium salt (8) (~267 mg, 0.78 mmol) dissolved in methanol was pipetted onto the ion-exchange resin. The post ion-exchange aqueous solution was collected below the burette and purified via ethyl acetate extractions to remove any unreacted tributylammonium tetrazoleazasydnone. The aqueous solution was evaporated under an air stream and dried in a desiccator over $P_2O_5$ yielding 117 mg (0.622 mmol, 79%) of 9.

(method B) The silver salt (7) (150 mg, 0.573 mmol) was added to an aqueous solution of hydroxylammonium chloride (0.95 equiv, 38 mg, 0.547 mmol). The mixture was stirred for two hours at 40° C. then filtered using 1 μm syringe filter and evaporated under an air stream, yielding (76 mg, 0.404 mmol, 71%) of (9). DSC: 130° C. (dec). IR: $\tilde{v}$=3063 (m), 2970 (m), 2946 (m), 2856 (m), 2717 (m), 2239 (w), 2188 (w), 1970 (w), 1764 (s), 1545 (m), 1505 (m), 1322 (m), 1256 (s), 1203 (s), 1180 (m), 1074 (m), 1023 (s), 984 (m), 831 (s), 743 (s), 735 (s), 629 (w), 572 (s) cm$^{-1}$. $^1$H NMR ([$D_6$]$D_2$O): δ=1.68 (s, 4H, $NH_4O^+$) ppm. $^{13}$C NMR ([$D_6$]$D_2$O): δ=166.8 (1C, —N=C—O—), 155.8 (1C, —N=C—N—) ppm. MS m/z: (ESI−) 154.1 ($C_2N_7O_2^-$), m/z: (ESI+) below limits of instrument ($NH_4O^+$). EA ($C_2H_4N_8O_3$, 188.11) calcd: C, 12.77; H, 2.14; N, 59.57%. Found: C, 7.56; H, 3.59; N, 38.63%. BAM impact: >40J. BAM friction: >360N.

Synthesis of Guanidinium 5-(5-oxido-1,2,3,4-oxatriazol-3-ium-3-yl)tetrazol-1-ide (10). The ion exchange resin was loaded with guanidinium hydrochloride following similar steps as the synthesis of 5. Tributylammonium salt (8) (~267 mg, 0.78 mmol) dissolved in methanol was pipetted onto the top of the resin and carefully pulled into the resin by lowering the water level. Once the methanolic solution was completely pulled into the resin, the burette was slowly filled with water without disturbing the resin. The burette solution was collected slowly dropwise (~7 seconds per drop). Impurities were extracted out of the aqueous solution with ethyl acetate extractions (3×20 ml). The aqueous solution was evaporated under an air stream and dried in a desiccator yielding 65 mg (0.304 mmol, 39%) of 10. Crystals were grown by slow evaporation from water. DSC: 130° C. (m.p.), 151° C. (dec.). IR: $\tilde{v}$=3336 (m), 3170 (m), 2164 (w), 1945 (w), 1800 (m), 1649 (s), 1597 (m), 1475 (m), 1360 (w), 1319 (s), 1261 (s), 1195 (m), 1183 (m), 1157 (m), 1080 (m), 1023 (m), 976 (m), 826 (w), 745 (m), 656 (m), 570 (w) cm$^{-1}$. $^1$HNMR ([$D_6$]$D_2$O): δ=6.60 (s, broad, 6H, —$NH_2$) ppm. $^{13}$C NMR ([$D_6$]$D_2$O): δ=167.2 (1C, —N=C—O—), 157.9 (1C, N2H5-C=NH), 155.9 (1C, —N=C—N—) ppm. MS m/z: (ESI−) 154.1 ($C_2N_7O_2^-$), m/z: (ESI+) 60.1 ($CH_6N_3^+$). EA ($C_3H_6N_{10}O_2$, 214.15) calcd: C, 16.83; H, 2.82; N, 65.41%. Found: C, 15.68; H, 3.49; N, 59.53%. BAM impact: >40J. BAM friction: >360N.

Attempted synthesis of Aminoguanidinium 5-(5-oxido-1,2,3,4-oxatriazol-3-ium-3-yl)tetrazol-1-ide (11). The aminoguanidinium salt (11) was made by two methods (A and B).

(method A) The ion exchange resin was loaded with aminoguanidinium hydrochloride following similar steps as the synthesis of 5. Tributylammonium salt (8) (~267 mg, 0.78 mmol) dissolved in methanol was pipetted onto the ion-exchange resin. The post ion-exchange aqueous solution was collected below the burette and purified via ethyl acetate extractions. After ethyl acetate extractions, the aqueous solution was evaporated under an air stream and dried in a desiccator yielding 81 mg of impure 11.

(method B) The silver salt (7) (330 mg, 1.26 mmol) was added to an aqueous solution of aminoguanidinium chloride (0.95 equiv, 132 mg, 1.19 mmol). The mixture was stirred for a few hours at 40° C. then filtered using 1 μm syringe filter and evaporated under an air stream, yielding 189 mg of impure 11. $^1$H NMR ([$D_6$]$D_2$O): δ=8.90 (s, 1H, —NH—$NH_2$), 7.23 (d, 2H, =$NH_2$), 6.75 (s, broad, 4H, —$NH_2$) ppm. $^{13}$C NMR ([$D_6$]$D_2$O): δ=167.1 (1C, —N=C—O—), 158.7 (1C, $N_2H_5$—C=NH), 158.1 (1C, —N=C—N—), 159.70 (1C, $CN_7$) ppm. MS m/z: (ESI−) 154.1 ($C_2N_7O_2^-$), 110.1 ($CN_7^-$), m/z: (ESI+) 75.1 ($CH_7N_4^+$). EA ($C_3H_7N_{11}O_2$, 229.16) calcd: C, 15.72; H, 3.08; N, 67.23%. Found: C, 9.34; H, 4.56; N, 50.72%.

Attempted synthesis of Triaminoguanidinium 5-(5-oxido-1,2,3,4-oxatriazol-3-ium-3-yl)tetrazol-1-ide (12). The triaminoguanidinium salt (12) was made by two methods (A and B).

(method A) The ion exchange resin was loaded with triaminoguanidinium hydrochloride following similar steps as the synthesis of 5. Tributylammonium salt (8) (~267 mg, 0.78 mmol) dissolved in methanol was pipetted onto the ion-exchange resin. The post ion-exchange aqueous solution was collected below the burette and purified via ethyl acetate extractions. After ethyl acetate extractions, the aqueous solution was evaporated under an air stream and dried in a desiccator yielding 61 mg of impure 12.

(method B) The silver salt (7) (200 mg, 0.764 mmol) was added to an aqueous solution of triaminoguanidinium chloride (0.95 equiv, 102 mg). The mixture was stirred for a few hours at 40° C. then filtered using 1 μm syringe filter and evaporated under an air stream, yielding 142 mg of impure 12. $^1$H NMR ([$D_6$]$D_2$O): δ=8.92 (s, 3H, NH—$NH_2$), 3.37 (s, broad, 6H, NH—$NH_2$) ppm. $^{13}$C NMR ([$D_6$]$D_2$O): δ=167.2 (1C, —N=C—O—), 159.4 (1C, $N_2H_5$—C=NH), 156.1 (1C, —N=C—N—), 159.79 (1C, $CN_5$) ppm. MS m/z: (ESI−) 154.1 ($C_2N_7O_2^-$), 110.1 ($CN_7^-$), m/z: (ESI+) 105.1 ($CH_9N_6^-$). EA ($C_3H_9N_{13}O_2$, 259.19) calcd: C, 13.90; H, 3.50; N, 70.25%. Found: C, 11.75; H, 4.29; N, 66.70%.

In one embodiment, the present disclosure provides a novel tetrazole azasydnone compound of Formula I:

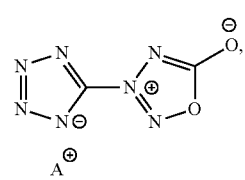

wherein $A^{\oplus}$ represents a cation with a 1+ charge.

In one embodiment regarding the novel tetrazole azasydnone compound of Formula I, wherein the cation is $H^+$, a metal cation, or a nitrogen-containing cation.

In one embodiment regarding the novel tetrazole azasydnone compound of Formula I, wherein the cation is $H^+$ or a silver cation.

In one embodiment regarding the novel tetrazole azasydnone compound of Formula I, wherein the compound of Formula I is used as a primary explosive.

In summary, several energetic salts of the novel tetrazole azasydnone (TAZ) were synthesized and characterized for their energetic properties. The metal-free compound 3 and silver salt 7 are potential replacements for primary explosives. Their energetic performances are comparable to in-service primary explosives (e.g. lead azide and lead styphnate) with the benefit of reduced toxicity. Specifically, the silver salt prepared during this study may be an interesting primary explosive due to its high sensitivity and demonstrated ability to undergo a deflagration to detonation transition.

Those skilled in the art will recognize that numerous modifications can be made to the specific implementations described above. The implementations should not be limited to the particular limitations described. Other implementations may be possible.

We claim:

1. A compound of Formula I:

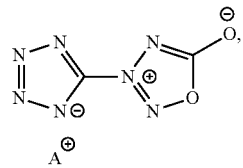

wherein $A^{\oplus}$ represents a cation with a $1^+$ charge.

2. The compound of claim 1, wherein the cation is $H^+$, a metal cation, or a nitrogen-containing cation.

3. The compound of claim 1, wherein the cation is $H^+$ or a silver cation ($Ag^+$).

4. The compound of claim 1, wherein the compound of claim 1 is used as a primary explosive.

* * * * *